(12) United States Patent
Aizenfeld et al.

(10) Patent No.: US 7,824,329 B2
(45) Date of Patent: *Nov. 2, 2010

(54) CONTROL SYSTEM FOR SUPPLYING FLUID MEDIUM TO ENDOSCOPE

(75) Inventors: Amram Aizenfeld, Kibbutz Ramot Menashe (IL); Victor Levin, Haifa (IL); Golan Salman, Tirat Hacarmel (IL); Omer Shezifi, Haifa (IL); Dan Oz, Even Yehuda (IL); Avi Levy, Herzylia (IL)

(73) Assignee: Stryker GI Ltd., Haifa (IL)

( * ) Notice: Subject to any disclaimer, the term of this patent is extended or adjusted under 35 U.S.C. 154(b) by 1134 days.

This patent is subject to a terminal disclaimer.

(21) Appl. No.: 11/207,092

(22) Filed: Aug. 18, 2005

(65) Prior Publication Data

US 2006/0052665 A1    Mar. 9, 2006

Related U.S. Application Data (60) Provisional application No. 60/606,976, filed on Sep. 3, 2004, provisional application No. 60/608,432, filed on Sep. 9, 2004.

(51) Int. Cl.
*A61B 1/12* (2006.01)
(52) U.S. Cl. .................. 600/158; 600/156; 600/159
(58) Field of Classification Search ................ 600/101, 600/118, 132, 136, 153, 155–159; 604/19, 604/23, 24, 26, 173
See application file for complete search history.

(56) References Cited

U.S. PATENT DOCUMENTS

| | | | | |
|---|---|---|---|---|
| 4,402,310 A | * | 9/1983 | Kimura | 600/158 |
| 4,548,197 A | * | 10/1985 | Kinoshita | 600/158 |
| 4,795,424 A | * | 1/1989 | Burner | 604/30 |
| 4,901,142 A | * | 2/1990 | Ikuno et al. | 348/69 |
| 5,098,387 A | | 3/1992 | Wiest | |
| 5,159,446 A | * | 10/1992 | Hibino et al. | 348/65 |
| 5,191,878 A | * | 3/1993 | Iida et al. | 600/157 |
| 5,243,967 A | * | 9/1993 | Hibino | 600/109 |
| 5,343,855 A | * | 9/1994 | Iida et al. | 600/157 |
| 5,402,770 A | * | 4/1995 | Iida et al. | 600/159 |
| 5,419,310 A | | 5/1995 | Frassica | |
| 5,562,652 A | * | 10/1996 | Davis | 604/890.1 |

(Continued)

FOREIGN PATENT DOCUMENTS

DE    37 16230 A1    11/1987

(Continued)

*Primary Examiner*—John P Leubecker
*Assistant Examiner*—Samuel Candler
(74) *Attorney, Agent, or Firm*—The Nath Law Group; Susanne M. Hopkins; Ari G. Zytcer (57) ABSTRACT

A control system for supplying fluid medium to an endoscopic apparatus which comprises an operation handle and an insertion tube provided with an insufflation channel, an irrigation channel and a suction channel extending therealong. The control system is provided with a system control unit with at least one source of a first fluid medium, with a source of a second fluid medium, with a source of vacuum and with a multifunctional connector for bringing the operation handle in fluid and electrical communication with the system control unit. The source of the first fluid medium and the source of the second fluid medium are simultaneously connectable to and disconnectable from the insufflation channel and the irrigation channel.

19 Claims, 4 Drawing Sheets

U.S. PATENT DOCUMENTS

| | | | |
|---|---|---|---|
| 5,609,563 A * | 3/1997 | Suzuki et al. | 600/118 |
| 5,746,694 A | 5/1998 | Wilk | |
| 5,916,145 A | 6/1999 | Chu | |
| 6,095,971 A * | 8/2000 | Takahashi | 600/159 |
| 6,096,008 A | 8/2000 | Korejwo | |
| 6,132,369 A * | 10/2000 | Takahashi | 600/159 |
| 6,239,909 B1 | 5/2001 | Hayashi | |
| 6,293,909 B1 | 5/2001 | Hayashi | |
| 6,309,347 B1 * | 10/2001 | Takahashi et al. | 600/159 |
| 6,387,045 B1 * | 5/2002 | Takahashi | 600/159 |
| 6,485,409 B1 | 11/2002 | Voloshin | |
| 6,558,317 B2 * | 5/2003 | Takahashi et al. | 600/158 |
| 7,335,159 B2 * | 2/2008 | Banik et al. | 600/156 |
| 7,413,543 B2 * | 8/2008 | Banik et al. | 600/129 |
| 7,678,044 B2 * | 3/2010 | Fujikura | 600/115 |
| 2001/0039370 A1 * | 11/2001 | Takahashi et al. | 600/159 |
| 2003/0018238 A1 * | 1/2003 | Obata et al. | 600/179 |
| 2004/0054258 A1 * | 3/2004 | Maeda et al. | 600/152 |
| 2004/0059283 A1 * | 3/2004 | Kirwan et al. | 604/23 |
| 2005/0131279 A1 * | 6/2005 | Boulais et al. | 600/141 |
| 2005/0154262 A1 * | 7/2005 | Banik et al. | 600/179 |
| 2005/0222499 A1 * | 10/2005 | Banik et al. | 600/132 |
| 2005/0245789 A1 * | 11/2005 | Smith et al. | 600/159 |
| 2005/0267333 A1 * | 12/2005 | Hino | 600/132 |
| 2006/0047184 A1 * | 3/2006 | Banik et al. | 600/156 |

FOREIGN PATENT DOCUMENTS

| | | |
|---|---|---|
| EP | 1077041 A1 * | 2/2001 |
| JP | 11123174 A * | 5/1999 |
| WO | WO 2004/016299 | 2/2004 |

* cited by examiner

CONTROL SYSTEM FOR SUPPLYING FLUID MEDIUM TO ENDOSCOPE

FIELD OF THE INVENTION

The present invention relates generally to the field of endoscopy and specifically to endoscopic apparatus used for colonoscopic procedures during which a flexible tube is inserted into the rectum and colon for examination of the colon interior for abnormalities. More particularly, the present invention refers to a control system for supplying a fluid medium, e.g. air, water etc. to the endoscope.

BACKGROUND OF THE INVENTION

There are known endoscopes employing inflatable flexible sleeves for propulsion endoscope within colon.

Voloshin (U.S. Pat. No. 6,485,409) discloses an endoscope, which comprises an endoscopic probe, a bending section for directing the probe within the colon (steering unit), an insertion tube and a flexible covering sleeve or a sheath, which is coupled proximally to the probe. The bending section of the endoscope is located behind the probe. The sleeve is attached to the endoscope in such a manner that its folded section is retained between a cap and an internal spindle, which are located between the insertion tube and the probe head. When inflated, the folded section unfolds over a flange of the internal spindle and an inner portion of the sleeve is pulled in a distal direction.

In PCT/IL03/00661 an endoscope is described which employs a flexible inflatable sleeve, which before inflation is retained within a dispenser. The dispenser employed in this endoscope has entry and exit ports defining a transit passage through which the endoscope may pass. The dispenser is adapted to capture the sleeve as the endoscope is retracted through the transit passage in a proximal direction. In another embodiment, the dispenser includes an external sleeve fixed to the dispenser and this external sleeve is adapted to be extended from the dispenser when the endoscope is retracted so that the external sleeve covers the flexible sleeve. By virtue of this provision any contamination on the flexible sleeve remains within the external sleeve and does not contact the endoscope or any other objects or areas outside the patient's body. After the endoscope has been removed entirely from the flexible sleeve, the dispenser together with the external sleeve is discarded.

It is mentioned in the above reference that the endoscope is provided with an internal sleeve, which is also known as multilumen tubing, since it is usually fitted with appropriate passages or lumens as required for irrigation, ventilation, suction and for passing endoscopic tools therethrough. To operate the endoscope, the proximal end of the multilumen tubing is detachably connected via a dedicated disposable connector, or so called hub, to a source of fluid medium, i.e. water, compressed air and vacuum. A fluid control system is provided, which comprises an external control unit with a pump for supplying compressed air, a flask for supplying water and a pump for producing vacuum. The control unit is provided also with several pinch valves, which control the supply of compressed air, water and vacuum to the multilumen tubing and compressed air to the inflatable sleeve.

Unfortunately maintenance of the endoscope provided with the above mentioned fluid control system is inconvenient and labor consuming, since before putting it into operation each tube should be connected one by one with a corresponding source of fluid medium.

The other disadvantage of the prior art control systems lies in the fact that it does not sufficiently prevent entrance of contaminated debris from the body channel back to the system.

SUMMARY OF THE INVENTION

The object of the present invention is, therefore, to provide a new and improved control system and system control unit for supplying fluid medium to the multilumen tubing and/or to the inflatable sleeve of an endoscope provided with such a sleeve.

A further object of the invention is to provide a new and improved system and system control unit, which is convenient and simple in operation and maintenance.

Still a further object of the invention is to provide a new and improved control system and system control unit, which reliably prevents entrance of contamination from the body channel during the endoscopic procedure.

For a better understanding of the present invention as well of its benefits and advantages, reference will now be made to the following description of its embodiments taken in combination with the accompanying drawings.

DETAILED DESCRIPTION OF THE INVENTION

Figure 1:
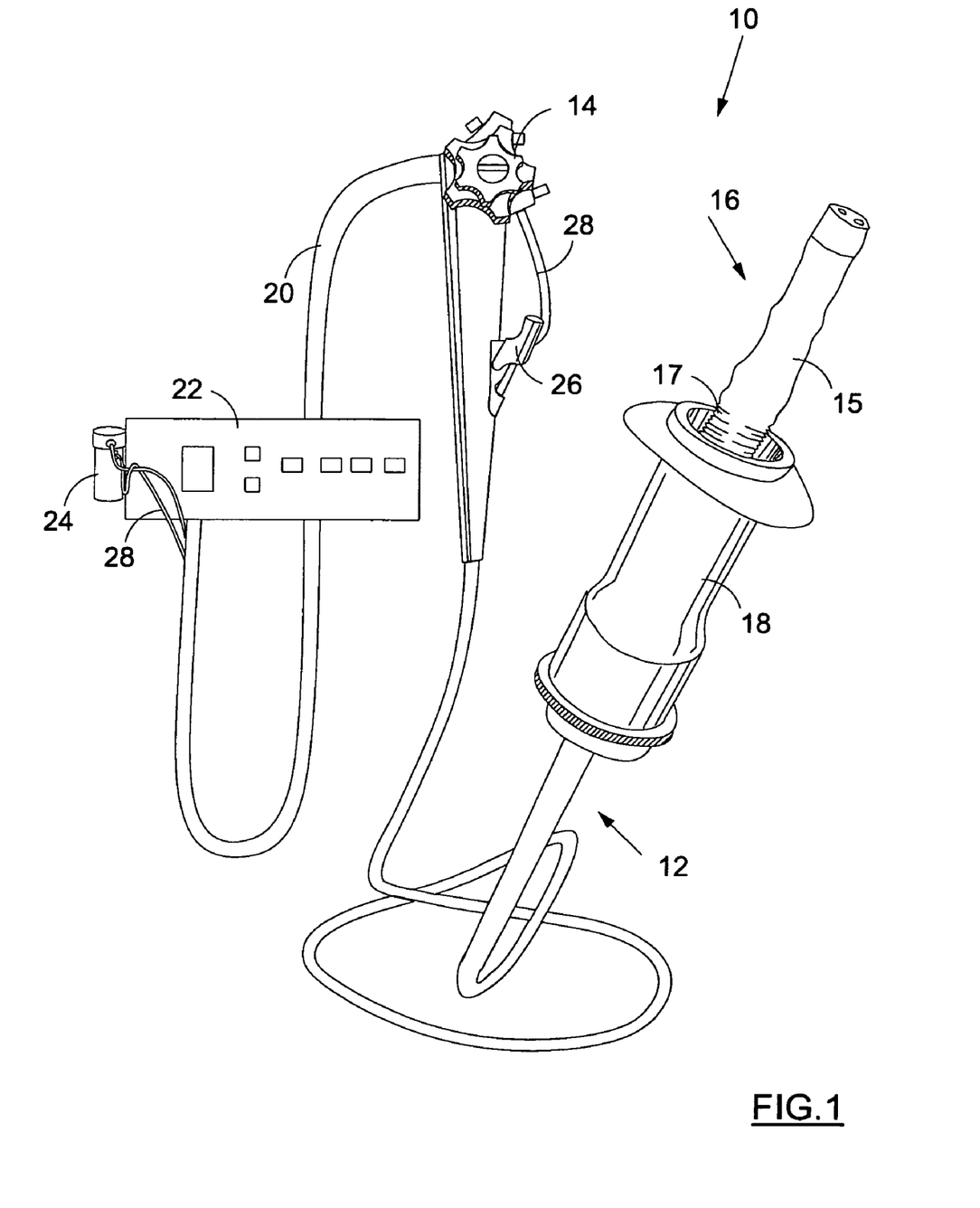
FIG. 1 depicts a general view of an endoscopic apparatus employing the control system of the invention.

With reference to FIG. 1 an endoscopic apparatus, preferably a colonoscopic apparatus 10, is shown with its following main components. The apparatus comprises an endoscope having an insertion tube with its proximal section 12 connected to an operation handle 14 and with its distal section 16 inserted in and protruding from a disposable dispenser 18. An example of such an apparatus and a general explanation of its construction and functioning can be found in the application PCT/IL03/00661 herein incorporated by reference.

It is shown also in FIG. 1 that a disposable inflatable sleeve covers the distal region of the endoscope. That part of the sleeve, which is seen in FIG. 1, comprises a frontal noninflatable portion 15 and a rear folded portion 17. The frontal portion covers the distal section of the endoscope and its head. The frontal portion does not inflate when the endoscope advances within the colon. The rear portion covers the insertion tube and unfolds when air or another fluid medium inflates the sleeve. By virtue of this provision the endoscope is propelled within the body passage. An explanation of this phenomenon can be found in the above referred-to reference. The endoscope, which can be used with the control system of the present invention, can be of similar type in the sense that it employs the same propelling mechanism, which is based on inflation of a flexible sleeve coupled to the endoscope's distal section. It should be appreciated, however, that the present invention is not limited merely to colonoscopy as such and to endoscopes, which are propelled by inflatable sleeve. It can be employed in any other endoscopic apparatus used for medical procedures requiring insertion of a probe in a body passage for inspection of its interior.

It is seen also in FIG. 1, that the handle is connected by an umbilical cord 20 to a system control unit (SCU) 22. Within the housing of the SCU there is provided a source of compressed air for inflating and venting the sleeve. Proximate to the system control unit, a flask 24 is provided, which is filled with water, to be supplied under pressure into the colon for irrigation. It is not shown specifically, but should be appreciated that appropriate tubes extend along the umbilical cord for supplying air for insufflation and for supplying vacuum produced by appropriate means (not shown in FIG. 1). The SCU is one of the main parts of the control system and it will be explained in more details in connection with FIGS. 2-4.

One should also bear in mind that within the insertion tube are provided various devices, which are necessary for functioning of the colonoscopic apparatus. These devices are known per se. Among such devices one can mention e.g. vertebrae and strings, which can be manipulated by the operation handle. It is not seen in FIG. 1, but should be appreciated, that along the colonoscope extends a multilumen tubing with appropriate passages for supplying water, as required for irrigation of the colon, air as required for insufflation and vacuum as required for suction. The multilumen tubing also allows introduction of surgical instruments into the colon as might be required during the colonoscopic procedure.

The multilumen tubing extends through the entire length of the endoscope, passes the handle and is connected to a dedicated Y-connector 26, which is detachably connectable to a lateral port provided on the handle, so as to connect the proximal end of the multilumen tubing with tubes 28 extending along the umbilical cord and supplying water and air from the SCU to the multilumen tubing.

In practice the multilumen tubing and the Y-connector are manufactured from plastic material. It would be advantageous if they are cheap, disposable items, which are discarded at the end of the endoscopic procedure after the colonoscope has been evacuated form the body passage. By virtue of this provision preparation to the new colonoscopic procedure is simple, convenient and fast and it is not associated with spreading of any contamination picked up from the body passage during the previous endoscopic procedure.

Figure 2:
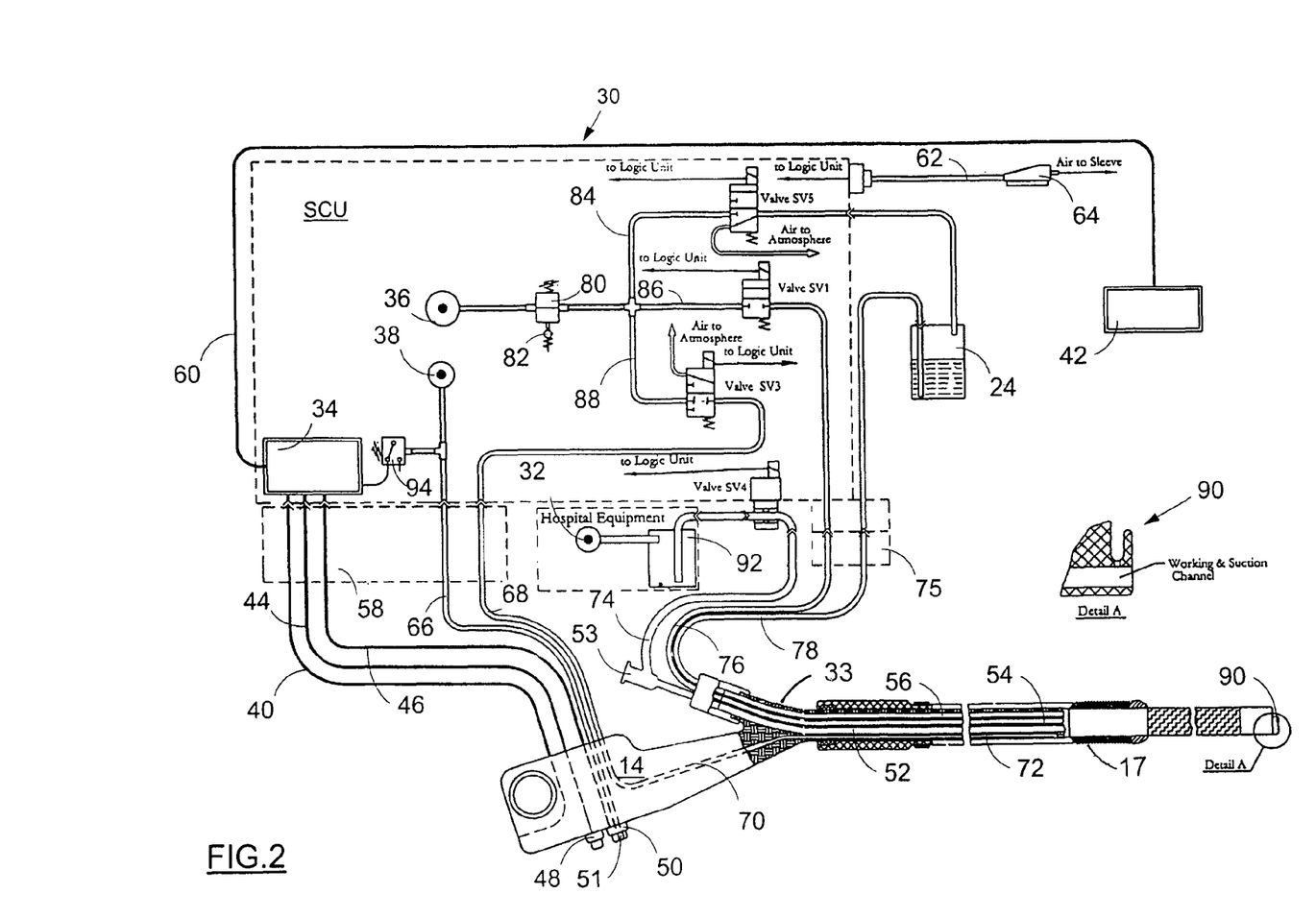
FIG. 2 depicts an embodiment of the control system and system control unit of the present invention

Referring now to FIG. 2 a first embodiment of the fluid control system of the invention is seen. The system is designated by reference numeral 30 and its main component, i.e. the SCU is designated schematically by a dotted line. The SCU controls supply of air, water and vacuum as required for proper functioning of the colonoscopic apparatus 10. Some external components of the fluid control system, namely flask 24 and vacuum pump unit 32, are also seen. In practice the flask volume should be sufficient to contain about 300 cc of water. As a suitable source of vacuum one could use available hospital equipment capable of producing a vacuum of −0.4 bar to enable suction from the body passage through the multilumen tubing with a flow rate of at least 20 liter per minute. The multilumen tubing is seen in FIG. 2 and it is designated by reference numeral 33.

Within the SCU are provided the necessary electronic, pneumatic and hydraulic components, e.g. a logic unit 34, a first and a second pump 36,38 for supplying compressed air and various valves as will be explained later on. It is not shown specifically but should be appreciated that appropriate power supply means can be also provided within the SCU as required for activation the valves and energizing the logic unit.

In practice the pump 36 should be capable to supply air under pressure 0.5-0.7 bar with a flow rate 3-5 liters per minute. This pump is intended to supply compressed air to the multilumen tubing, to the inflatable sleeve and to the flask.

The pump 38 should be capable of supplying air under pressure 0.3 bar with a flow rate 2 liter per minute. This pump is intended for supplying air to the operating handle. The operating handle has an opening for releasing the air. The purpose of this arrangement will be explained further.

The logic unit 34 is electrically connected by a line 40 to auxiliary control buttons provided on the handle 14 (not seen). The auxiliary control buttons might be available for controlling a video signal supplied to a monitor 42, e.g. for saving or freezing the displayed picture.

The logic unit is also electrically connected by signal lines 44, 46 to respective control buttons 48 and 50 provided on the handle. The button 48 enables controlling of suction through a channel 52 made in the multilumen tubing. This channel functions either as a suction channel (when vacuum is supplied therethrough) or as a working channel when it is required to insert a surgical tool through a port 53. The button 50 enables supply of air to the body passage through a dedicated insufflation channel 54. This button also enables the supply of water to the body passage through a dedicated irrigation channel 56. A through going opening 51 is provided in the button 50. This opening can be closed or opened by the doctor's finger during operating of the handle. The through going opening is in flow communication with the pump 38. For connecting the SCU with lines 40, 44 and 46 a detachable multifunctional connector 58 is provided. This connector is multifunctional in the sense that it enables not only passing electrical signals between the SCU and control buttons 48,50 and auxiliary control buttons, but also ensures supplying of compressed air to the handle. The logic unit 34 is electrically connected by a line 60 with the monitor and by a line 62 to a foot pedal 64, which upon pressing generates a signal, which triggers inflation of the sleeve. The connection of line 62 to the logic unit is schematically designated in FIG. 2 by an arrow with the label "to logic unit".

In FIG. 2 are also seen tubes 66,68, which allow flow communication between the SCU and the handle. The tubes are detachably connected to the SCU by virtue of the same multifunctional connector 58. It is seen that tube 66 serves for supplying pressurized air from pump 38 to opening 51 in the button 50. It is also seen that tube 68 supplies pressurized air from pump 36 to the handle. Within the handle there is provided a passage 70 through which compressed air from pump 36 proceeds to a channel 72 extending through the insertion tube for inflating the sleeve.

It is shown also in FIG. 2 that the multilumen tubing is in flow communication with the SCU via tubes 74,76,78, which are connected to the Y-connector 26 provided at the lateral extension of the handle. These tubes respectively supply vacuum to the working channel 52, air to the insufflation channel 54 and water to the irrigation channel 56. A common connector 75 is provided for simultaneous bringing in fluid communication of tube 76 with pump 36 and tube 78 with flask 24. In accordance with one of the aspects of the present invention tubes 76,78 are immediately connectable and disconnectable to the respective source of air and water without the necessity to connect/disconnect the tubes one by one by separate connectors dedicated to each line. This provision renders the setting up of the system very simple, convenient and fast. It is not shown specifically but should be appreciated that the common connector could be arranged at the flask, e.g. in its cover.

Within the SCU are mounted various hydraulic and pneumatic components of the system, which are necessary for controlling supply of the fluid medium to the colonoscope. The fluid medium is supplied by the following supply lines: line a) for supplying of compressed air from pump 36 to the sleeve, to the multilumen tubing and to the flask; line b) for supplying vacuum produced by vacuum pump 32 to the multilumen tubing; line c) for supplying of compressed air from pump 38 to the handle; and line d) for supplying of water from flask 24 to the multilumen tubing.

It is seen, for example, that in the line a) there is provided a pressure regulator 80 with a safety valve 82 for keeping the pressure supplied by pump 36 within a narrow range of 0.5-0.7 bar. The pressurized air proceeds via three ducts 84,86,88 to three normally shut off solenoid valves SV5, SV1 and SV3. These valves, when opened, enable supply of pressurized air from the pump either to flask 24, or to line 76, or to line 68. As soon as pressurized air is supplied to the flask, water within the flask is urged to proceed via tube 78 to the irrigation channel of the multilumen tubing so as to be ejected therefrom by means of a sprinkler means 90 provided at the forwardmost end of the colonoscope. In practice water is ejected from the flask with a flow rate of at least 1 cc per second. It can be readily appreciated that pressure is not permanently maintained within the flask, but only when it is required to supply water for irrigation.

In the line b) there is provided a suction bottle 92 and a suction valve SV4, which is a conventional pinch valve capable of selectively releasing the tube 74 passing therethrough. Pressing suction button 48 on the handle 14 actuates this pinch valve.

It should be appreciated that all valves are electrically connected to the logic unit and are controlled thereby.

In the line c) there is provided a pressure sensor 94, which senses air pressure in the line 66. The pressure sensor is electrically connected to the logic unit and as soon as the air pressure in line 66 reduces below a certain preset level the sensor generates and sends to the logic unit a signal. Upon receiving this signal the logic unit opens valve SV1 and pressurized air is supplied via line 76 to the insufflation channel of the multilumen tubing.

The control system depicted in FIG. 2 operates as follows.

When it is required to inflate the sleeve, one should press foot pedal 64. Upon pressing the pedal, an electrical signal is transferred to the logic unit, which, in its turn, generates a signal for opening the normally shut-off valve SV3. When this valve opens, pressurized air is allowed to proceed from pump 36 to the sleeve via passage 70 in the handle and then via passage 72 in the insertion tube. In order to release pressure from the sleeve, one should release the pedal after evacuating the colonoscope from the body channel. In this situation, a signal is generated by the logic unit to close valve SV3 so as to enable release of pressure from tube 68 to the atmosphere.

When suction is required, one should press button 48. Upon pressing this button, a signal will be generated by the logic unit to open pinch valve SV4 and then vacuum will be allowed to proceed to the body cavity via tube 74 and suction channel 52.

For insufflation, one should close opening 51 provided on the control button 50. This causes an increase of pressure in line 66, which will be detected by pressure sensor 94. Accordingly the logic unit opens solenoid valve SV1 and pressurized air will be allowed to proceed from pump 36 through tube 76 to the insufflation channel.

It should be kept in mind that instead of opening 51 being closeable by a doctor's finger for triggering the air supply from pump 38, one could use a different arrangement, e.g. electrical two stroke switch.

To irrigate the body cavity one should deeply press control button 50. Then a signal will be generated by the logic unit to open valve SV5. Upon opening the valve, pressurized air is allowed to enter the flask and thus water is urged to proceed to the irrigation channel via tube 78. When there is no signal, the pressure is released from the valve immediately to the atmosphere and there is no pressure in the flask.

It should be readily appreciated that control buttons 48,50 are merely electrical switches, which are electrically connected to the logic unit and there is no flow communication between the buttons and the multilumen tubing. By virtue of this provision the danger of contaminating the buttons by any debris penetrating from the body channel or cavity is prevented. At the same time, since flow of air is permanently maintained in the direction from pump 38 to opening 51 it is possible to retain the same mode of carrying out the insufflation or irrigation, to which the doctors are so accustomed. In accordance with this mode a finger pressure on the hole in the center of button 50 provides insufflation and further depression of the button triggers the irrigation.

It should be also appreciated that, since the control buttons operate the valves electrically and not mechanically, there is no need for mechanical parts, like pistons etc. In the prior art systems the control buttons usually are associated with a mechanical control mechanism comprising mechanical parts. Due to inevitable contamination it is required to dismantle the control mechanism and to clean it after each colonoscopy session. In the present invention the buttons are not associated with any mechanical parts, which could get contaminated.

Figure 3:
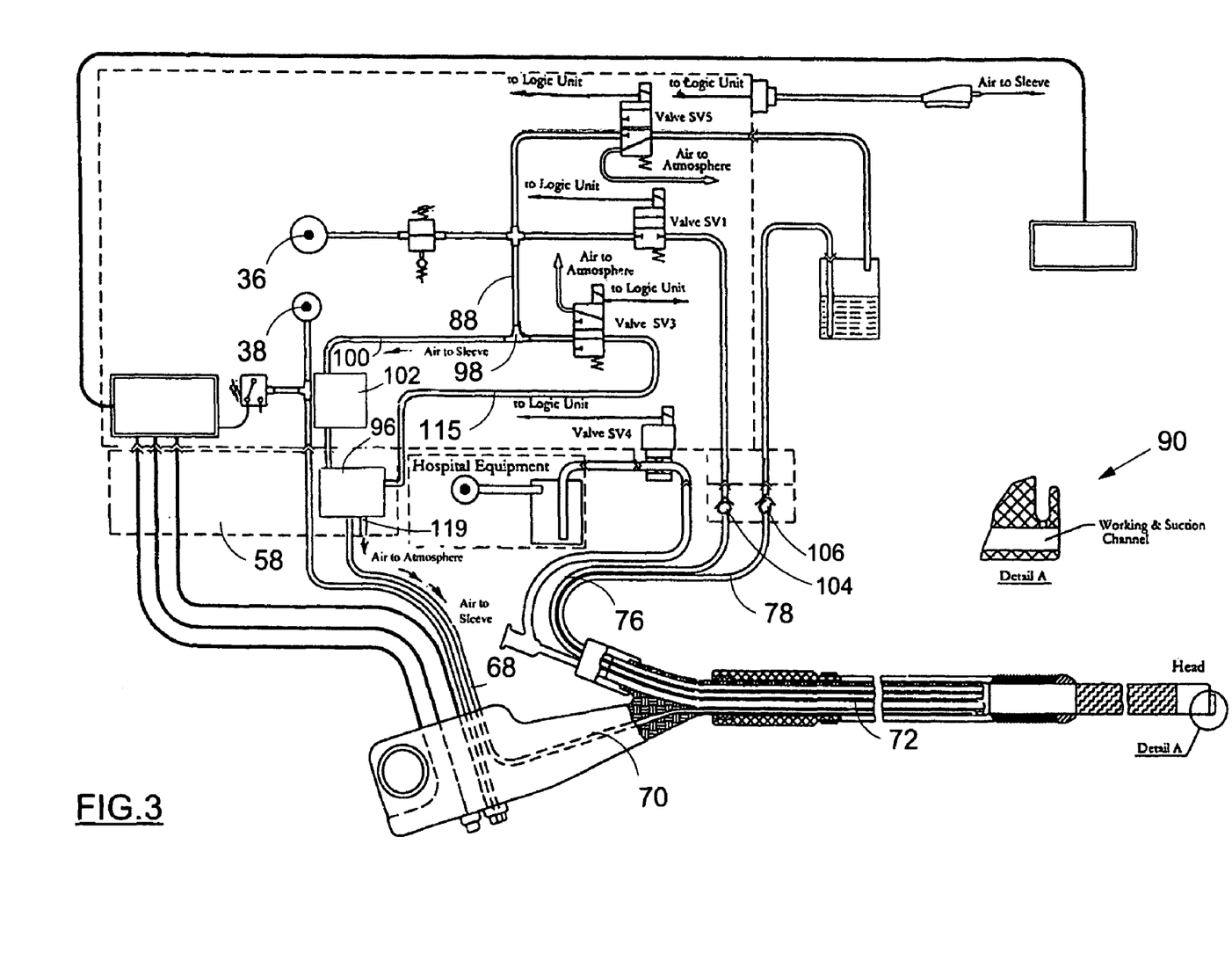
FIG. 3 depicts a second embodiment of the control system and system control unit of the present invention
Figure 4:
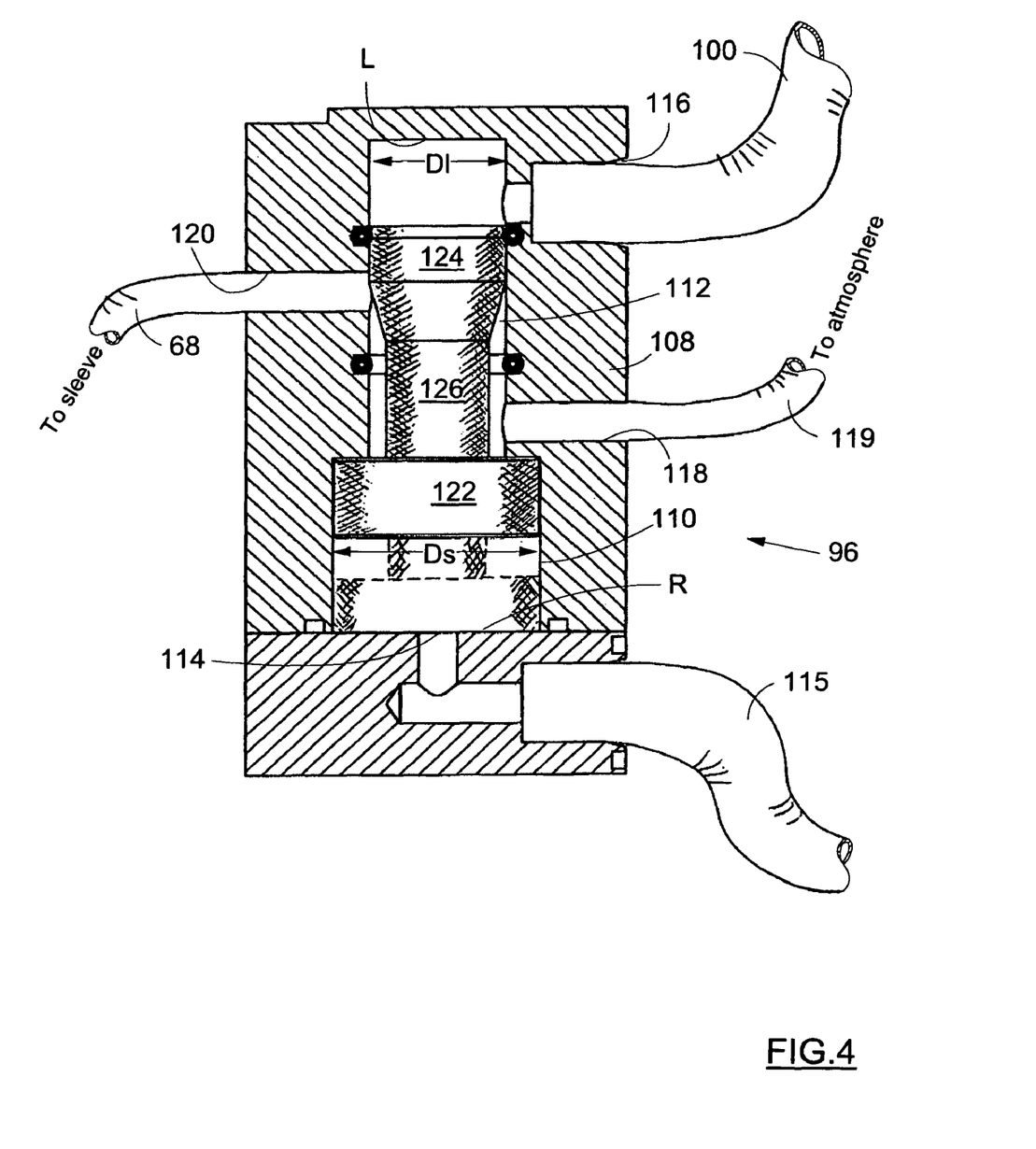
FIG. 4 is a sectional view, depicting a contamination trap employed in the control system of the present invention.

Now a second embodiment of the present invention will be explained. This embodiment is depicted in FIG. 3 and FIG. 4 and it is intended to reduce as much as possible the probability of contamination from the body passage through the sleeve when it becomes punctured. Referring to FIG. 3 it is seen that most of the components of the system remain the same, however in contrast to the previous embodiment in the supply line a) there is provided a contamination trap means 96, which is located between the handle and valve SV3. In practice it would be preferable if the trap means resides within the connector 58 as seen in FIG. 3.

The trap means is intended to prevent entrance of any contamination back to the SCU when flow communication is provided between the body channel or cavity and the SCU via channel 72, passage 70 and tube 68. Construction and functioning of the trap means will be explained in more details with reference to FIG. 4.

Referring again to FIG. 3 it is also seen that duct 88 splits at a knee 98 to form a lateral duct 100, leading to the trap means. Situated between the knee and the trap means a flow meter 102 is provided. This flow meter is required to detect the situation when the sleeve is damaged, e.g. punctured and it is required to terminate the inflation. It would be advantageous if in addition to the flow meter a manometer is provided to monitor any changes of pressure within the sleeve.

It is also seen that lines 76 and 78 are provided with dedicated check valves 104,106. By virtue of this provision passing of flow medium is permitted only in one direction, i.e. from the SCU and from the flask to the multilumen tubing while backward flow is prevented. By virtue of this provision it is possible to keep contamination from the inside of the SCU and the flask.

It should be appreciated that the elements of the above disclosed control system can be employed not only in a colonoscope, which is fitted with an inflatable covering sleeve. They can be used in the control system of any other endoscope, in which it is required to supply fluid medium to the insertion tube.

Referring to FIG. 3 and FIG. 4 it is seen that trap means 96 is, in fact, a control valve, which is designed as a spool valve comprising a cylindrical housing 108 with residing therein a double piston, which design will be discussed further. Longitudinally extending along the housing a cylindrical bore is provided, which is defined by a short section 110, a long section 112, a right end R and a left end L. The inside diameter of the short section is Ds, while the inside diameter of the long section is Dl and it is seen that Ds is larger than Dl. At the right end of the bore there is provided a port 114 which is in fluid communication with a control line 115, through which compressed air is supplied from pump 36 via valve SV3. This air controls the position of the double piston within the housing. It should be appreciated, that in the embodiment of the control system, which is shown in FIG. 3 the valve SV3 operates as a normally open valve. It is seen in FIG. 4, that on the peripheral wall of the long section 112 there are provided three ports 116,118,120. The port 116 is located close to the left end of the bore This port is intended to be in fluid communication with the lateral duct 100, through which compressed air is supplied to the trap means. The port 118 is located at the right of the middle of the long section and it is connected immediately to the atmosphere by a line 119. The port 120 is located at the left of the middle of the long section and its is intended to be in fluid communication with tube 68, through which compressed air is supplied from the trap to the sleeve. Within the housing the double piston is displaceable between the opposite ends L and R of the bore. The double piston comprises a first cylinder 122, an opposite second cylinder 124 and a rod 126, on which the cylinders are secured. The first cylinder is deployed within the short section 110 of the bore and its diameter is very close to the inside diameter Ds. The second cylinder is deployed within the long section 112 of the bore and its diameter is very close to the inside diameter Dl.

An O-ring or other suitable sealing is provided between each cylinder and the cylindrical periphery wall of the respective bore section. By virtue of this provision a fluid-tight engagement is ensured between the first and the second cylinder and the respective periphery wall of the bore when the piston slides reciprocatingly along the bore. The control system in accordance with this embodiment operates as follows. In a situation, when there is no need to inflate the sleeve and/or a fluid medium should be released therefrom, the normally-opened valve SV3 allows compressed air to proceed from pump 36 via control line 115 to port 114 and to displace the piston to a left position, which is shown in FIG. 4 by solid lines. It can be seen that in this position the first cylinder is abutted by the left end of the short section of the bore. The piston will retain in this position all the time when there is no signal from the logic unit to valve SV3. The length of the rod and of the cylinders as well as particular location of ports 116,118 and 120 is selected in such a manner, that when the piston is retained in the left position, cylinder 124 prevents flow communication between port 116 and ports 120, 118. Accordingly compressed air cannot proceed from duct 100 to the sleeve. At the same time, fluid medium is allowed to proceed from the sleeve to the trap (via port 120) and then to be released from the trap to atmosphere (via port 118). It should be appreciated that fluid medium releasing from the sleeve might be contaminated, however the SCU is fully prevented from being contaminated, since there is no fluid communication between ports 120,118 and ports 116,114. Furthermore, compressed air, which enters the trap means via port 116, also contributes to preventing the entrance of contaminating debris to the SCU.

It would be advantageous to provide duct 100 with an auxiliary venting port, which would be located in vicinity of the trap or in the trap itself. Such a port would permanently release the air in the line to the atmosphere and this might reduce the probability of contaminating the SCU in the situation when the sleeve is deflated more than one time during the same endoscopy session.

In the situation, when it is required to inflate the sleeve, one should press foot pedal 64 and the logic unit will generate an appropriate signal for closing valve SV3. In this situation compressed air is released from the valve to the atmosphere and there is no pressure acting on the cylinder 122. Compressed air enters the trap via port 116 and acts on cylinder 124 so as to displace the double piston in the right position, which is shown in FIG. 4 by dotted lines. In this position port 116 is in fluid communication with port 120 and therefore compressed air is allowed to proceed from pump 36 to the sleeve.

It should be appreciated that the invention is not limited to the above-described embodiments and that one ordinarily skilled in the art can make modifications or changes without deviating from the scope of the invention, as will be defined in the appended claims.

When used in the following claims, the meaning of terms "comprise", "include", "have" and their conjugates is "including but not limited to".

It should also be appreciated that the features disclosed in the foregoing description, and/or in the following claims, and/or in the accompanying drawings may, both separately and in any combination thereof, be material for realizing the present invention in diverse forms thereof.

The invention claimed is:

1. A control system supplying a fluid medium to an endoscopic apparatus comprising an operation handle and an insertion tube, the control system comprising:
   a system control unit comprising
      at least one source of a first fluid medium,
      hydraulic and pneumatic components configured to facilitate fluid transmission of the first fluid medium to the insertion tube comprising an insufflation channel, a suction channel and an irrigation channel, each extending separately along the entire length of the insertion tube, and
      a logic unit configured to control the hydraulic and pneumatic components;
   a source of a second fluid medium;
   a vacuum source;
   a singular detachable multifunctional connector for effecting direct fluid and electrical communication between the operation handle of the apparatus and the system control unit, the singular detachable multifunctional connector configured to attach and detach from the system control unit; and
   a common connector capable of being separately disconnected from the multifunctional connector, whereby the at least one source of the first fluid medium and the source of the second fluid medium are simultaneously connectable to and disconnectable from the insufflation channel and the irrigation channel.

2. The control system according to claim 1, wherein the insertion tube comprises a multilumen tubing, and the insufflation channel, the irrigation channel and the suction channel extend along the entire length of the multilumen tubing.

3. The control system according to claim 1, wherein the at least one source of the first fluid medium comprises a pump for supplying compressed air, the source of the second fluid medium comprises a container filled with water and the vacuum source comprises a vacuum pump.

4. The control system according to claim 3, wherein the at least one source of the first fluid medium comprises a first pump for supplying compressed air to the insufflation channel and a second pump for supplying compressed air to the operation handle.

5. The control system according to claim 4, wherein the operation handle comprises a control button provided with an opening, wherein upon closure thereof compressed air is supplied to the insufflation channel by the first pump.

6. The control system according to claim 5, wherein the second pump is in fluid communication with the opening.

7. The control system according to claim 6, wherein the second pump is in fluid communication with the opening via a pressure sensor.

8. The control system according to claim 4, wherein the endoscopic apparatus is provided with an inflatable covering sleeve, the insertion tube being fitted with a channel for inflating the sleeve and the first pump being connected to the channel for inflating the sleeve.

9. The control system according to claim 8, wherein the hydraulic and pneumatic components comprise normally closed valves, which are respectively located between the first pump and between the insufflation channel, the receptacle and the channel for inflating the sleeve.

10. The control system according to claim 8, comprising a means for trapping contamination located between the first pump and the channel for inflating the sleeve.

11. The control system according to claim 10, wherein the multifunctional connector further comprises the means for trapping.

12. The control system according to claim 10, wherein the means for trapping comprises a spool valve.

13. The control system according to claim 3, wherein the first pump is connected to the insufflation channel and to the container.

14. The control system according to claim 3, further comprising a first check valve located between the first pump and the insufflation channel and a second check valve located between the container and the irrigation channel.

15. The control system according to claim 1, wherein the multifunctional connector enables passing electrical signals between the system control unit and control buttons on the operation handle, and also ensures supply of fluid medium to the operation handle.

16. A method for controlling supply of air into an insufflation channel extending along the entire length of an operating handle and extending along the entire length of an insertion tube of an endoscopic apparatus, the method comprising:
    providing a system control unit, in electrical and fluid communication with the operating handle, the system control unit comprising
        a first pump for producing compressed air supplied to the insufflation channel,
        hydraulic and pneumatic components enabling supply of compressed air to the insufflation channel,
        a second pump for producing compressed air and being connected by a line to the operating handle, and
        a logic unit controlling the hydraulic and pneumatic components;
    providing a singular detachable multifunctional connector for effecting direct fluid and electrical communication between the operation handle of the apparatus and the system control unit, the singular detachable multifunctional connector configured to attach and detach from the system control unit; and
    providing a common connector capable of being separately disconnected from the multifunctional connector;
    providing a control button at the operating handle, the control button having an opening which is in flow communication with the second pump; and
    generating a signal for activating the hydraulic and pneumatic components to establish fluid communication between the first pump and the insufflation channel, wherein the signal is generated by the logic unit upon terminating flow communication between the opening and the second pump.

17. The method for controlling supply of air according to claim 16, wherein the hydraulic and pneumatic components comprise at least one normally closed valve located between the first pump and the insufflation channel, the valve being openable upon receiving the signal.

18. The method for controlling supply of air according to claim 17, further comprising sensing pressure in a line between the second pump and the operating handle and generating the signal upon an increase of pressure up to a certain level.

19. The method for controlling supply of air according to claim 16, wherein terminating flow communication between the second pump and the opening comprises closing the opening using a finger.

* * * * *